(12) United States Patent
Smith

(10) Patent No.: US 10,244,760 B2
(45) Date of Patent: *Apr. 2, 2019

(54) OPHTHALMIC AND CONTACT LENS SOLUTIONS CONTAINING SIMPLE SACCHARIDES AS PRESERVATIVE ENHANCERS

(71) Applicant: FXS Ventures, LLC, Salem, NH (US)

(72) Inventor: Francis X. Smith, Salem, NH (US)

(73) Assignee: FXS VENTURES, LLC, Salem, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,203

(22) Filed: Jan. 26, 2018

(65) Prior Publication Data

US 2018/0146678 A1 May 31, 2018

Related U.S. Application Data

(63) Continuation of application No. 15/278,660, filed on Sep. 28, 2016, now Pat. No. 9,913,474, which is a continuation-in-part of application No. 11/613,029, filed on Dec. 19, 2006, now Pat. No. 9,492,582, which is a continuation-in-part of application No. 10/544,151, filed as application No. PCT/US01/46344 on Nov. 8, 2001, now Pat. No. 9,492,581.

(60) Provisional application No. 60/246,870, filed on Nov. 8, 2000.

(51) Int. Cl.
| | | |
|---|---|---|
| *A01N 47/44* | (2006.01) | |
| *C11D 3/00* | (2006.01) | |
| *C11D 3/48* | (2006.01) | |
| *A61L 12/14* | (2006.01) | |
| *A61K 9/00* | (2006.01) | |
| *C11D 3/04* | (2006.01) | |
| *C11D 3/20* | (2006.01) | |
| *C11D 3/22* | (2006.01) | |
| *C11D 3/37* | (2006.01) | |
| *A61K 47/26* | (2006.01) | |

(52) U.S. Cl.
CPC ............ *A01N 47/44* (2013.01); *A61K 9/0048* (2013.01); *A61K 47/26* (2013.01); *A61L 12/141* (2013.01); *A61L 12/142* (2013.01); *A61L 12/143* (2013.01); *A61L 12/145* (2013.01); *C11D 3/0078* (2013.01); *C11D 3/046* (2013.01); *C11D 3/2065* (2013.01); *C11D 3/221* (2013.01); *C11D 3/3703* (2013.01); *C11D 3/48* (2013.01)

(58) Field of Classification Search
CPC ..................................................... A01N 47/44
See application file for complete search history.

(56) References Cited

U.S. PATENT DOCUMENTS

| | | |
|---|---|---|
| 6,139,646 A | 10/2000 | Asgharian et al. |
| 6,162,393 A | 12/2000 | De Bruiju et al. |
| 6,617,291 B1 | 9/2003 | Smith |

FOREIGN PATENT DOCUMENTS

| | | |
|---|---|---|
| EP | 0923950 | 6/1999 |
| JP | 10-108899 | 4/1998 |
| JP | 20000084052 A | 3/2000 |
| WO | WO0007634 | 2/2000 |
| WO | WO0238161 | 5/2002 |

*Primary Examiner* — Zohreh A Fay
(74) *Attorney, Agent, or Firm* — Peter J. Mikesell; Christopher E. Blank; Schmeiser, Olsen & Watts, LLP

(57) ABSTRACT

The present invention relates to an ophthalmic solution comprising 0.00001 to 10.0 weight percent of a simple saccharide, at least 0.00001 weight percent of a preservative, and not more than about 0.2 percent by weight chloride. The simple saccharide is chosen from the group consisting of: inositol; mannitol; sorbitol; sucrose; dextrose; glycerin; propylene glycol; ribose; triose; tetrose; erythrose; threose; pentose; arabinose; ribulose; xylose; xylulose; lyxose; hexose; allose; altrose; fructose; galactose; glucose; gulose; idose; mannose; sorbose; talose; tagatose; adlose; ketose; heptose; sedoheptulose; monosaccharides; disaccharides; sugar alcohols; xylitol; and polyol.

20 Claims, No Drawings

OPHTHALMIC AND CONTACT LENS SOLUTIONS CONTAINING SIMPLE SACCHARIDES AS PRESERVATIVE ENHANCERS

CROSS-REFERENCE TO RELATED APPLICATIONS

This application is a continuation of U.S. patent application Ser. No. 15/278,660 (filed Sep. 28, 2016) which is a continuation-in-part of U.S. patent application Ser. No. 11/613,029 (filed Dec. 19, 2006) which is a continuation-in-part of U.S. patent application Ser. No. 10/544,151 (filed Aug. 1, 2005) which is a national stage entry of International Patent Application PCT/US01/46344 (filed Nov. 8, 2001) which claims the benefit of U.S. Provisional Patent Application 60/246,870 (filed Nov. 8, 2000). The content of each of these applications is hereby incorporated by reference.

FIELD OF THE INVENTION

The present invention relates to the field of ophthalmic solutions and their uses. In particular the invention relates to contact lens cleaning solutions, contact lens rinsing and storing solutions, solutions to deliver active pharmaceutical agents to the eye, solutions for disinfecting ophthalmic devices and the like.

BACKGROUND

The present invention relates to the field of ophthalmic solutions and especially to the aspects of preservative efficacy and comfort after prolonged use. These ophthalmic solutions have been used for some period of time and are available as over the counter products. Solutions that are used in direct contact with corneal tissue such as the delivery of an active pharmaceutical agent to the eye, or indirectly, such as the cleaning, conditioning or storage of devices that will come in contact with corneal tissue, such as contact lenses, there is a need to ensure that these solution do not introduce sources of bacterial or other microbial infection. Thus preservatives are included to reduce the viability of microbes in the solution and to lessen the chance of contamination of the solution by the user since many of the solutions are bought, opened, used, sealed and then reused. State of the art preservative agents include polyhexamethylene biguanide (PHMB) POLYQUAD™, chlorhexidine and benzalkonium chloride, and the like, all of which at some concentration irritate corneal tissue and lead to user discomfort. Therefore, a solution that employs a given amount of a preservative agent, but which is made more effective by addition of an agent that is not a preservative agent would be desired.

SUMMARY OF THE INVENTION

The present invention relates to improved ophthalmic solutions that employ inositol and other simple saccharides in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

More specifically, the invention relates to an ophthalmic solution comprising 0.00001 to 10.0 weight percent of a simple saccharide, at least 0.00001 weight percent of a preservative, and not more than about 0.2 percent by weight chloride. The simple saccharide may be chosen from the group consisting of: inositol; mannitol; sorbitol; sucrose; dextrose; glycerin; propylene glycol; ribose; triose; tetrose; erythrose; threose; pentose; arabinose; ribulose; xylose; xylulose; lyxose; hexose; allose; altrose; fructose; galactose; glucose; gulose; idose; mannose; sorbose; talose; tagatose; adlose; ketose; heptose; sedoheptulose; monosaccharides; disaccharides; sugar alcohols; xylitol; and polyol.

The solutions specifically described herein have 0.00001 to about 10.0 percent of simple saccharides in combination with other active ingredients useful in ophthalmic solutions such as buffers, preservatives, surfactants, and antimicrobial agents, and with a low chloride concentration, not more than about 0.2 percent by weight. It has been found, surprisingly that inositol, and other sugars including mannitol, sorbitol, sucrose, dextrose, glycerin and propylene glycol, effectively increase the antibacterial effect of preservatives in low salt (low chloride) conditions.

The preservatives that are specifically useful are include polyhexamethylene biguanide (PHMB), POLYQUAD™, chlorhexidne, and benzalkonium chloride, as well as other cationic preservatives that may prove useful in the present invention as well. The cationic preservatives are used at effective amounts as preservatives, and in the instance of PHMB from 0.0001 percent by weight to higher levels of about 0.01 weight percent. Specifically, the cationic polymeric preservative includes polymeric biguanides such as polymeric hexamethylene biguanides (PHMB), and combinations thereof Such cationic polymeric biguanides, and water-soluble salts thereof, having the following formula:

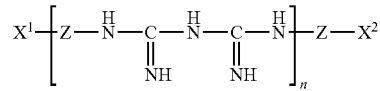

wherein Z is an organic divalent bridging group which may be the same or different throughout the polymer, n is on average at least 3, preferably on average 5 to 20, and $X^1$ and $X^2$ are

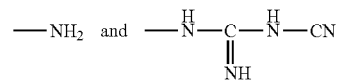

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Avecia (Wilmington, Del.) under the trademark COSMOCIL™ CQ. Such polymers and water-soluble salts are referred to as polyhexamethylene (PHMB)

or polyaminopropyl biguanide (PAPB). The term polyhexamethylene biguanide, as used herein, is meant to encompass one or more biguanides have the following formula:

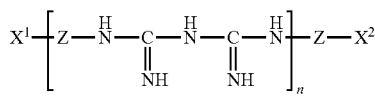

wherein Z, $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated. Preferably, the water-soluble salts are compounds where n has an average value of 2 to 15, most preferably 3 to 12.

It was found that an unexpected preservative efficacy was displayed when inositol was used in conjunction with the cationic preservative. The other components of the solution are used at levels known to those skilled in the art in order to improve the wearability of lenses and when used directly in the eye, to provide increased resistance to infection. Inositol used in ophthalmic solutions increases preservative efficacy in certain formulations, provides increased resistance to infection in corneal tissue, in certain formulations, and improves the quality of tears in certain formulations.

The formulations may also include buffers such as phosphate, bicarbonate, citrate, borate, ACES, acetate, BES, BICINE, BIS, BIS-Tris, BIS-Tris Propane, bicarbonate, histidine, HEPES, Tris, HEPPS, imidazole, MES, MOPS, PIPES, TAPS, TES, glycine, tiomethamine, and Tricine.

Surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold by BASF under the trademark CREMOPHOR®.

Inositol, mannitol, sorbitol, sucrose, dextrose, glycerin, propylene glycol and the other agents used in the present invention are all commercially available, and well enough understood to be formulated into products within the scope of the invention by those skilled in the art.

The solutions of the present invention may contain other additives including but not limited to buffers, tonicity agents, demulcents, wetting agents, preservatives, sequestering agents (chelating agents), surface active agents, and enzymes.

Other aspects include adding to the solution from 0.001 to 1 weight percent chelating agent (preferably disodium EDTA) and/or additional microbicide, (preferably 0.00001 to 0.1 or 0.0000 1 to 0.01) weight percent polyhexamethylene biquanide (PHMB, N-alkyl-2-pyrrolidone, chlorhexidine, polyquaternium-1, hexetidine, bronopol, alexidine, low concentrations of hydrogen peroxide, and ophthalmologically acceptable salts thereof.

Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether) in N,N,N',N' tetraacetic acid (EGTA), aminodiacetic acid and hydroxyethylamino diacetic acid. These acids can be used in the form of their water soluble salts, particularly their alkali metal salts. Especially preferred chelating agents are the di-, tri- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.0 to 7.6. Significant deviations from neutral (pH 7.3) will cause changes in the physical parameters (i.e. diameter) in some contact lenses. Low pH (pH less than 5.5) can cause burning and stinging of the eyes, while very low or very high pH (less than 3.0 or greater than 10) can cause ocular damage.

The additional preservatives employed in the present invention are known, such as polyhexamethylene biguanide, N-alkyl-2-pyrrolidone, chlorhexidine, polyhexamethylenebiguanide, alexidine, polyquatemium- 1, hexetidine, bronopol and a very low concentration of hydrogen peroxide, e.g., 30 to 200 ppm.

The solutions of the invention are compatible with both rigid gas permeable and hydrophilic contact lenses during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof. The tonicity of the solution is typically adjusted to approximately 240 milliosmoles per kilogram solution (mOsm/kg) to render the solution compatible with ocular tissue and with hydrophilic contact lenses. In one embodiment, the solution contains 0.01 to 0.2 weight percent sodium chloride. The important factor is to keep the concentrations of such additives to a degree no greater than that would supply a chloride concentration of no greater than about 0.2 mole percent.

Suitable viscosity inducing agents can include lecithin or the cellulose derivatives such as hydroxymethytcellulose, hydroxypropylcellulose, hydroxypropyl methylcellulose (HPMC), and methylcellulose in amounts similar to those for surfactants, above.

EXAMPLE 1

An example of a formulation containing low salt, a buffer and cationic preservative follows:

| Log Reduction | Buffer | Preservative | Preservative Enhancer | Wetting Agent |
|---|---|---|---|---|
| 2.27 | none | PHMB 0.0001% | None | None |
| 3.85 | Bis-Tris Propane 0.2% | PRMB 0.0001% | None | CREMOPHOR ®RH 40 |
| 4.00 | Bis-Tris Propane 0.2% | PHMB 0.0001% | propylene glycol 3% | CREMOPHOR ®RH 40 |
| 4.40 | Bis-Tris Propane 0.2% | PHMB 0.0001% | sorbitol 5% | CREMOPHOR ®RH 40 |
| 4.40 | Bis-Tris Propane 0.2% | PHMB 0.0001% | inositol 5% | CREMOPHOR ®RH 40 |
| 2.98 | OPTI-FREE ® Express | | | |
| 0.68 | Ciba SOLO-CARE ® | | | |
| 2.99 | B&L RENU ® MULTIPLUS MPS ® | | | |

Column 1 shows the reduction of *C. albicans* at 2 hours using a typical antibacterial test. The data shows improved activity over the preservative alone; improved activity over the buffer control without sugar additive and improved activity over commercially available products

EXAMPLE 2

Data Table

| Log Reduction | Buffer | Preservative | Additive |
|---|---|---|---|
| 2.53 | None | PHMB 0.0001% | none |
| 1.34 | Bis-Tris Propane 0.2% | PHMB 0.0001% | sodium chloride 0.5% |
| 3.42 | Bis-Tris Propane 0.2% | PHMB 0.0001% | glycerin 0.5% |
| 2.73 | Bis-Tris Propane 0.2% | PHMB 0.0001% | propylene glycol 05% |
| 1.13 | Bis-Tris Propane 0.2% | PHMB 0.0001% | potassium chloride 0.5% |
| 3.92 | Bis-Tris Propane 0.2% | PHMB 0.0001% | sorbitol 0.5% |
| 3.23 | Bis-Tris Propane 0.2% | PHMB 0.0001% | mannitol 0.5% |
| 3.06 | Bis-Tris Propane 0.2% | PHMB 0.0001% | inositol 0.5% |
| 3.72 | Bis-Tris Propane 0.2% | PHMB 0.0001% | dextrose 0.5% |

This data shows that the antimicrobial activity of buffer with the sugar or glycol is greater than the preservative alone and that decreased activity at 0.5% sodium chloride or 0.5% potassium chloride solutions occurs as well. Thus the surprising effect of the sugar derived preservative enhancers is displayed and the effects relationship to chloride concentration is demonstrated.

EXAMPLE 3

Solutions with a cationic polymeric preservative (PHMB) sodium chloride and glycerin and a buffer were made as shown in the following table and the preservative efficacy was measured.

| Log Reduction | Buffer | Preservative | Sodium Chloride | Glycerin |
|---|---|---|---|---|
| 1.69 | none | PHMB 0.0001% | none | none |
| 1.74 | none | PHMB 0.0001% | 0.1% | none |
| 1.46 | none | PHMB 0.0001% | 0.2% | none |
| 0.86 | none | PHMB 0.0001% | 0.4% | none |
| 0.49 | none | PHMB 0.0001% | 0.5% | none |
| 2.44 | Bis-Tris Propane 0.2% | PHMB 0.0001% | none | none |
| 1.89 | Bis-Tris Propane 0.2% | PHMB 0.0001% | 0.1% | none |
| 1.54 | Bis-Tris Propane 0.2% | PHMB 0.0001% | 0.2% | none |
| 0.98 | Bis-Tris Propane 0.2% | PHMB 0.0001% | 0.4% | none |
| 0.89 | Bis-Tris Propane 0.2% | PHMB 0.0001% | 0.5% | none |
| 2.46 | Bis-Tris Propane 0.2% | PHMB 0.0001% | none | 0.20% |
| 2.41 | Bis-Tris Propane 0.2% | PHMB 0.0001% | none | 0.50% |

The above date illustrates the effect of sodium chloride on preservative efficacy and the effect of glycerin in improving preservative efficacy in low salt solutions.

EXAMPLE 4

Solutions were made according to methods described supra with sodium phosphate as the buffer.

| Log Reduction | Buffer | Preservative | Tonicity Agent |
|---|---|---|---|
| 0.79 | Sodium Phosphate 0.2% | PHMB 0.0001% | none |
| 0.33 | Sodium Phosphate 0.2% | PHMB 0.0001% | Sodium Chloride 0.7% |

This data illustrates the problem with sodium chloride is independent of buffer type.

EXAMPLE 5

Solutions were formulated with sodium chloride, sorbitol and sucrose and then lenses were immersed in the resultant solutions and chlorhexidine gluconate was added. The lenses were exposed for 3 hours and the amount of the chlorhexidine deposited on the lens was measured.
Method: HPLC analysis for chlorhexidine gluconate
3.0 mL solution exposed to 1/2 lens
Matrix: 1 ppm CHG/0.2% Bis-Tris Propane/0.1% CREMOPHOR® RH 40

Lens: Freshlook ColorBlends (45% phemfilcon A, 55% water) Wesley Jess

| Additive | μg CHG per lens | % Decrease |
|---|---|---|
| None | 4.0 | 67.3% |
| Sodium Chloride | 3.6 | 59.3% |
| Sorbitol | 3.0 | 50.7% |
| Sucrose | 1.3 | 21.4% |

This test shows that the sugars used in the test have an ability to decrease the extent of preservative binding for of cationic preservatives when properly formulated. Both sorbitol and sucrose solutions demonstrated efficacy in reducing preservative deposition.

EXAMPLE 6

The following experiment demonstrates the effect of chloride concentration on the antimicrobial effectiveness of PHMB preservative solutions.

| Log Reduction | Buffer | Preservative | NaCl | Additive | Effect |
|---|---|---|---|---|---|
| 1.05 | Bis-Tris 0.2% | PHMB 0.0001% | None | none | 54% |
| 1.47 | Bis-Tris 0.2% | PHMB 0.0001% | None | None | 75% |
| 0.77 | Bis-Tris 0.2% | PHMB 0.0001% | 0.70% | None | 39% |
| 2.36 | Bis-Tris Propane 0.2% | PHMB 0.0001% | None | None | 123% |
| 2.32 | Bis-Tris Propane 0.2% | PHMB 0.0001% | None | None | 119% |
| 0.91 | Bis-Tris Propane 0.2% | PHMB 0.0001% | 0.70% | None | 47% |
| 1.27 | Tricine 0.2% | PHMB 0.0001% | None | None | 65% |
| 1.31 | Tricine 0.2% | PHMB 0.0001% | None | None | 67% |
| 0.62 | Tricine 0.2% | PHMB 0.0001% | 0.70% | none | 32% |

EXAMPLE 7

Formulations containing inositol (Spectrum) were prepared in a 0.2% phosphate buffer. The solutions were made isotonic with sodium chloride and preserved with polyhexamethylene biquanide at 0.0001%. The pH was adjusted to 7.2 with either 1 N sodium hydroxide or 1 N hydrochloric acid. The in vitro microbicidal activity of the solutions was determined by exposing *C. albicans* to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Additive | 4 hour log reduction |
|---|---|
| Inositol (0.5%) | 1.1 |
| Buffer control | 0.8 |

The solution containing inositol showed an improvement in the activity against *C. albicans* as compared to the buffer control.

EXAMPLE 8

Formulation Preserved Solution for rinsing, storage, reconstituting enzyme tablets. A formulation was prepared by dissolving Tricine, Allantoin, Inositol, Disodium edetate, and Polyoxyl 40 Hydrogenated Castor Oil in 80% of the water volume. The pH of the solution was adjusted to 7.3 with 1 N sodium hydroxide. The tonicity of the solution was adjusted with sodium chloride and polyhexamethylene biguanide was added. The solution was diluted to volume with water.

| Constituent | Supplier | % Weight/Volume | Amount |
|---|---|---|---|
| Purified water | | to 80% | 40 mL |
| Tricine | Spectrum | 1.0% | 0.500 g |
| Allantoin | Spectrum | 0.25% | 0.125 g |
| Inositol | Spectrum | 0.1% | 0.050 g |
| Edetate Disodium | Spectrum | 0.055% | 0.0275 g |
| Polyoxyl 40 Hydrogenated Castor Oil | CREMOPHOR ® RH 40 from BASF Co. | 0.1% | 0.5 mL of 10% |
| Sodium Hydroxide, 1N | | as required for pH adjustment to 7.3 | as required for pH adjustment to 7.3 |
| Purified Water | | to 98% | Dilute to 49 mL |
| Sodium Chloride | Fisher | As required for tonicity adjustment 285 mOsm | As required for tonicity adjustment 285 mOsm |
| Polyhexamethylene-biguanide HCl | 20% w/w solution available under the mark COSMOCIL ™ CQ from Avecia | 0.0001% | 50 μL of 0.1% |
| Purified Water | | Balance to 100% | Dilute to 50 mL |

This provides an example of a specific formulation of the present invention but does not fully illustrate the bounds or limits of the invention.

What is claimed is:

1. A method for providing an ophthalmic solution comprising:

contacting an eye with a single-part solution comprising 0.00001 to 10.0 weight percent of a simple saccharide selected from a group consisting of an aldose, a triose, a tetrose, a pentose, a hextose, and a heptose;

at least 0.00001 weight percent of a preservative with a structure given by:

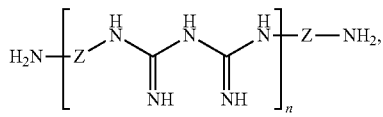

wherein n is a number between 1 and 500 and Z is a divalent bridging group; and wherein the concentration of chloride in said solution is not more than 0.2 percent by weight.

2. The method as recited in claim 1, wherein the concentration of the preservative is between 0.1 and 100 parts per million.

3. The method as recited in claim 2, wherein the preservative is polyhexamethylene biguanide.

4. The method as recited in claim 1, wherein the single-part solution further comprises a physiologically compatible buffer.

5. The method as recited in claim 4, wherein the physiologically compatible buffer is selected from a group consisting of: phosphate, bicarbonate, citrate, borate, ACES, acetate, BES, BICINE, BIS, BIS-Iris, BIS-Iris Propane, bicarbonate, histidine, HEPES, Iris, HEPPS, imidazole, MES, MOPS, PIPES, TAPS, TES, glycine, tromethamine, and Tricine.

6. The method as recited in claim 1, wherein the single-part solution further comprises a wetting agent.

7. The method as recited in claim 6, wherein the wetting agent is selected from a group consisting of: polysorbate surfactants, polyoxyethylene surfactants, polyethoxylated glycerides, phosphonates, saponins and polyethoxylated castor oils.

8. The method as recited in claim 1, wherein the single-part solution further comprises a sequestering agent.

9. The method as recited in claim 8, wherein the sequestering agent selected from a group consisting of: ethylenediaminetetraacetic acid, phosphonates, citrate, gluconate, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether), tetraacetic acid (EGTA), aminodiacetic acid, hydroxyethylamino diacetic acid, tartarate, and water-soluble salts thereof.

10. The method as recited in claim 1, wherein the simple saccharide is an aldose.

11. The method as recited in claim 1, wherein the simple saccharide is triose.

12. The method as recited in claim 1, wherein the simple saccharide is a tetrose.

13. The method as recited in claim 1, wherein the simple saccharide is erythrose or threose.

14. The method as recited in claim 1, wherein the simple saccharide is a pentose.

15. The method as recited in claim 1, wherein the simple saccharide is arabinose, ribulose, xylose, xylulose, lyxose or xylitol.

16. The method as recited in claim 1, wherein the simple saccharide is a ketose.

17. The method as recited in claim 1, wherein the simple saccharide is a hextose.

18. The method as recited in claim 1, wherein the simple saccharide is inositol, ribose, allose, altrose, fructose, galactose, glucose, gulose, idose, mannose, sorbose, talose or tagatose.

19. The method as recited in claim 1, wherein the simple saccharide is a heptose.

20. The method as recited in claim 1, wherein the simple saccharide is sedoheptulose.

* * * * *